US011304900B1

(12) United States Patent
Shade et al.

(10) Patent No.: US 11,304,900 B1
(45) Date of Patent: *Apr. 19, 2022

(54) TRANSPARENT COLLOIDAL VITAMIN SUPPLEMENT BLEND

(71) Applicant: Quicksilver Scientific, Inc., Lafayette, CO (US)

(72) Inventors: Christopher W. Shade, Lafayette, CO (US); Steven Tieu, Lafayette, CO (US)

(73) Assignee: Quicksilver Scientific, Inc., Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/902,842

(22) Filed: Jun. 16, 2020

Related U.S. Application Data

(63) Continuation of application No. 16/215,049, filed on Dec. 10, 2018, now Pat. No. 10,722,465.

(60) Provisional application No. 62/596,297, filed on Dec. 8, 2017.

(51) Int. Cl.
| | | |
|---|---|---|
| *A61K 9/00* | (2006.01) | |
| *A61K 9/51* | (2006.01) | |
| *A61K 9/107* | (2006.01) | |
| *A61K 9/127* | (2006.01) | |
| *A61K 47/44* | (2017.01) | |
| *A61K 8/67* | (2006.01) | |
| *A61K 31/375* | (2006.01) | |
| *A61K 31/51* | (2006.01) | |
| *A61K 31/355* | (2006.01) | |
| *A61K 31/122* | (2006.01) | |
| *A61K 31/07* | (2006.01) | |
| *A61K 31/593* | (2006.01) | |
| *A61K 31/525* | (2006.01) | |
| *A61K 31/455* | (2006.01) | |
| *A61K 31/4415* | (2006.01) | |
| *A61K 31/714* | (2006.01) | |

(52) U.S. Cl.
CPC ............ *A61K 9/127* (2013.01); *A61K 9/1075* (2013.01); *A61K 9/1277* (2013.01); *A61K 31/07* (2013.01); *A61K 31/122* (2013.01); *A61K 31/355* (2013.01); *A61K 31/375* (2013.01); *A61K 31/4415* (2013.01); *A61K 31/455* (2013.01); *A61K 31/51* (2013.01); *A61K 31/525* (2013.01); *A61K 31/593* (2013.01); *A61K 31/714* (2013.01)

(58) Field of Classification Search
CPC ........ A61K 9/127; A61K 47/44; A61K 9/107; A61K 9/006; A61K 9/08; A61K 49/0084; A61K 47/543; A61K 9/1075; A61K 31/355; A61K 2300/00; A61K 45/06; A61K 8/676; A61K 8/11; A61K 31/375; A61K 8/06; A61K 8/675; A61K 9/10; A61K 9/0053; A61K 9/51

See application file for complete search history.

(56) References Cited

U.S. PATENT DOCUMENTS

| | | |
|---|---|---|
| 5,238,683 A | 8/1993 | Crystal |
| 5,260,065 A | 11/1993 | Mathur et al. |
| 5,395,619 A | 3/1995 | Zalipsky et al. |
| 5,565,439 A | 10/1996 | Piazza et al. |
| 5,569,464 A | 10/1996 | Endo et al. |
| 5,711,965 A | 1/1998 | Ghyczy et al. |
| 5,817,695 A | 10/1998 | Pellico |
| 5,834,014 A | 11/1998 | Weiner et al. |
| 5,871,769 A | 2/1999 | Fleming et al. |
| 5,935,588 A | 8/1999 | Afriat et al. |
| 6,048,886 A | 4/2000 | Neigut |
| 6,143,786 A | 11/2000 | Gohman et al. |
| 6,159,500 A | 12/2000 | Demopoulos et al. |
| 6,180,662 B1 | 1/2001 | Lanzendorfer et al. |
| 6,204,248 B1 | 3/2001 | Demopoulos et al. |
| 6,218,436 B1 | 4/2001 | Howard et al. |
| 6,235,271 B1 | 5/2001 | Luther et al. |
| 6,245,797 B1 | 6/2001 | Winokur |
| 6,287,611 B1 | 9/2001 | Morello et al. |
| 6,319,517 B1 | 11/2001 | Cavallo et al. |
| 6,337,065 B1 | 1/2002 | Jacobson et al. |
| 6,358,516 B1 | 3/2002 | Harod |
| 6,492,410 B1 | 12/2002 | Leopold et al. |
| 6,534,540 B2 | 3/2003 | Kindness et al. |
| 6,562,369 B2 | 5/2003 | Luo et al. |
| 6,596,305 B1 | 7/2003 | Edgerly-Plug |
| 6,630,157 B1 | 10/2003 | Horrobin et al. |

(Continued)

FOREIGN PATENT DOCUMENTS

| | | |
|---|---|---|
| EP | 0834301 | 4/1998 |
| WO | WO 9111117 | 8/1991 |

(Continued)

OTHER PUBLICATIONS

Farina et al, Metals, Oxidative Stress and Neurodegeneration: A focus on Iron, Manganese and Mercury, Neurochem Int., Apr. 2013, 62(5): 575-594.

Kale et al, Emulsion Micro Emulsion and Nano Emulsion: A Review, Systematic Reviews in Pharmacy, Sys Rev Pharm. 2017; 8(1): 39-47.

Arno Hazekamp, The Trouble with CBD Oil, S. Karger AG, Basel, Med Cannabis Cannabinoids 2018;1:65-72.

(Continued)

*Primary Examiner* — Tracy Liu

(74) *Attorney, Agent, or Firm* — Blanchard & Associates

(57) ABSTRACT

An aqueous, intra-oral, transparent nanoemulsion blend in the form of a stable dispersion delivers both oil- and water-soluble components of a vitamin supplement in the desired concentrations to the cells of a mammal when orally administered. The transparent nanoemulsion blend includes at least two different bilayer water-core liposome components and at least one monolayer surfactant bound particle component. The transparent nanoemulsion blend optionally may include a micelle formed from phosphatidylcholine (PC).

57 Claims, 3 Drawing Sheets

(56) References Cited

U.S. PATENT DOCUMENTS

| | | |
|---|---|---|
| 6,713,533 B1 | 3/2004 | Panzner |
| 6,764,693 B1 | 7/2004 | Smith |
| 7,825,084 B2 | 11/2010 | Harris et al. |
| 8,067,381 B1 | 11/2011 | Harris et al. |
| 8,114,913 B1 | 2/2012 | Guilford et al. |
| 8,147,869 B2 | 4/2012 | Guilford et al. |
| 8,252,325 B2 | 8/2012 | Guilford et al. |
| 8,349,359 B2 | 1/2013 | Guilford et al. |
| 8,679,530 B2 | 3/2014 | Guilford et al. |
| 8,741,373 B2 | 6/2014 | Bromley et al. |
| 9,474,725 B1 | 10/2016 | Reillo et al. |
| 9,730,911 B2 | 8/2017 | Verzura et al. |
| 9,839,612 B2 | 12/2017 | Reillo et al. |
| 9,925,149 B2 | 3/2018 | Kaufman |
| 9,972,680 B2 | 5/2018 | Reillo et al. |
| 9,974,739 B2 | 5/2018 | Reillo et al. |
| 10,016,389 B2 | 7/2018 | Zhang |
| 10,084,044 B2 | 9/2018 | Reillo et al. |
| 10,103,225 B2 | 10/2018 | Reillo et al. |
| 10,239,808 B1 | 3/2019 | Black et al. |
| 2002/0025313 A1 | 2/2002 | Micklus et al. |
| 2002/0048551 A1 | 4/2002 | Keller et al. |
| 2002/0102316 A1 | 8/2002 | Weissman |
| 2002/0106339 A1 | 8/2002 | Fisher et al. |
| 2002/0132781 A1 | 9/2002 | Kindness et al. |
| 2002/0137785 A1 | 9/2002 | Kindness et al. |
| 2002/0169195 A1 | 11/2002 | Kindness et al. |
| 2002/0182585 A1 | 12/2002 | Kindness et al. |
| 2002/0187130 A1 | 12/2002 | Kindness et al. |
| 2003/0059462 A1 | 3/2003 | Barenholz et al. |
| 2003/0083241 A1 | 5/2003 | Young |
| 2003/0096000 A1 | 5/2003 | Solis et al. |
| 2003/0162829 A1 | 8/2003 | Kindness et al. |
| 2003/0157220 A1 | 9/2003 | Morello et al. |
| 2004/0022841 A1 | 2/2004 | Hassan et al. |
| 2004/0022873 A1 | 2/2004 | Guilford et al. |
| 2004/0127476 A1 | 7/2004 | Kershman et al. |
| 2004/0170560 A1 | 9/2004 | Fossheim et al. |
| 2004/0219123 A1 | 11/2004 | Astruc et al. |
| 2005/0131041 A1 | 6/2005 | Salman et al. |
| 2005/0191343 A1 | 9/2005 | Liang |
| 2006/0099244 A1 | 5/2006 | Guilford et al. |
| 2006/0106093 A1 | 5/2006 | Rich et al. |
| 2007/0065456 A1 | 3/2007 | Woods |
| 2008/0131496 A1 | 6/2008 | Guilford et al. |
| 2008/0207679 A1 | 8/2008 | Berkowitz |
| 2009/0047340 A1 | 2/2009 | Guilford et al. |
| 2009/0068253 A1 | 3/2009 | Guilford et al. |
| 2009/0069279 A1 | 3/2009 | Astruc et al. |
| 2010/0086573 A1 | 4/2010 | Anderson |
| 2010/0166846 A1 | 6/2010 | Guilford et al. |
| 2010/0173882 A1 | 7/2010 | Giliyar et al. |
| 2010/0233193 A1 | 9/2010 | Guilford et al. |
| 2010/0233297 A1 | 9/2010 | Guilford et al. |
| 2010/0291196 A1 | 11/2010 | Guilford et al. |
| 2010/0316700 A1 | 12/2010 | Guilford et al. |
| 2011/0020436 A1 | 1/2011 | Guilford et al. |
| 2011/0129523 A1 | 6/2011 | Guilford et al. |
| 2011/0274625 A1 | 11/2011 | Redelmeier et al. |
| 2011/0305752 A1 | 12/2011 | Guilford et al. |
| 2012/0087994 A1 | 4/2012 | Guilford et al. |
| 2012/0135068 A1 | 5/2012 | Guilford et al. |
| 2012/0141608 A1 | 6/2012 | Guilford et al. |
| 2012/0171280 A1 | 7/2012 | Zhang |
| 2012/0219616 A1 | 8/2012 | Guilford et al. |
| 2012/0282325 A1 | 11/2012 | Tong et al. |
| 2013/0045271 A1 | 2/2013 | Dadey et al. |
| 2013/0231297 A1 | 9/2013 | Krawitz |
| 2014/0161784 A1 | 6/2014 | Westerlund et al. |
| 2015/0079156 A1 | 3/2015 | Kett et al. |
| 2015/0296856 A1 | 10/2015 | Chandra et al. |
| 2016/0166516 A1 | 6/2016 | Gannon et al. |
| 2016/0263047 A1 | 9/2016 | Kaufman et al. |
| 2017/0127712 A1 | 5/2017 | Yiannios |
| 2018/0263283 A1 | 9/2018 | Popplewell et al. |

FOREIGN PATENT DOCUMENTS

| | | |
|---|---|---|
| WO | WO 98/55075 | 12/1998 |
| WO | WO 01/26618 | 4/2001 |
| WO | WO 2008/100629 | 8/2008 |
| WO | WO 2012/066334 | 5/2012 |
| WO | WO 2016/020485 | 2/2016 |

OTHER PUBLICATIONS

Tan et al, Tocotrienols Vitamin E Beyond Tocopherols, CRC Press, Tocotrienols Second Edition, Sec. 2.3, Nov. 16, 2016.

Amory et al, Oral Testosterone in Oil Plus Dutasteride in Men: A Pharmacokinetic Study, The Endocrine Society, J. Clin of Endocrinol Metab, May 2005, 90(5):2610-2617.

Peter Casson, MD, Delivery of dehydroepiandrosterone to premenopausal women: Effects of micronization & nonoral administration, Feb. 1996, 649-653.

Dilova et al., Increasing the Solubility of a Poor Soluble API-milk Thistle dry extract (Silymarin), Pharmacia, vol. 61, No. 1/2014.

TRANSPARENT COLLOIDAL VITAMIN SUPPLEMENT BLEND

REFERENCE TO RELATED APPLICATIONS

This application is a continuation of U.S. Nonprovisional application Ser. No. 16/215,049, filed Dec. 10, 2018, entitled "Transparent Colloidal Vitamin Supplement," which claims the benefit of U.S. Provisional Application No. 62/596,297 entitled "Transparent Colloidal Vitamin Supplement" filed Dec. 8, 2017, both of which are incorporated by reference in the entirety.

BACKGROUND

Negative health and disease states are associated with vitamin deficiency. Optimal vitamin concentrations are required by the body to properly eliminate toxins from the body, promote the proper functioning of the digestive and cardiovascular systems, and provide a feeling of wellness. In addition to formal deficiency, an over consumption of one vitamin can produce an out of balance condition creating a deficiency in another vitamin, even if that vitamin is not formally low. Enhanced concentrations of some vitamins are also known to reduce or eliminate the symptoms of some chronic conditions.

Vitamin A is oil-soluble and plays a vital role in bone growth, reproduction, and immune system health. It also helps the skin and mucous membranes repel bacteria and viruses more effectively. Vitamin A is essential to healthy vision, and may slow declining retinal function in people with retinitis pigmentosa.

The B complex vitamins are water-soluble and include Vitamins B1-B3, B5-B7, B9, and B12. The B complex vitamins assist in converting food into energy and in repairing and maintaining tissues and cellular structures.

Vitamin D3 is oil-soluble and assists the body in absorbing calcium and phosphorous and helps to prevent bone disorders. The body makes Vitamin D when exposed to sunlight.

Vitamin C (ascorbic acid) is water-soluble and serves as an antioxidant that deactivates free radicals, and thus assists in repairing and building tissues. When taken orally in larger doses, including the upper limit of 2,000 mg per day, Vitamin C can result in acid reflux.

Vitamin E is oil-soluble includes the tocotrienols (alpha, beta, gamma, and delta isomers) and the tocopherols (alpha, beta, gamma, and delta isomers), which are all oil-soluble. All tocotrienol and tocopherol isomers (thus, all forms of Vitamin E) have some antioxidant activity due to an ability to donate a hydrogen atom (a proton plus electron) to an oxygen radical—thus deactivating the radical by forming an —OH (alcohol) group. The critical chemical structural difference between the tocotrienol and tocopherol forms of Vitamin E is that the tocopherols have saturated side chains, while the tocotrienols have unsaturated isoprenoid side chains with three double bonds. The different tocotrienol isomers demonstrate different bioavailability and efficacy depending on the type of antioxidant performance being measured. Conventionally, alpha-tocopherol has been the preferred form of "Vitamin E", as this oil-soluble tocopherol isomer is credited with having the highest antioxidant biological activity and is preferentially absorbed and accumulated in humans when orally consumed.

Vitamins K1 and K2 are oil-soluble and are essential for helping the body respond to injuries. K1 and K2 are active in regulating blood clotting and assisting in the transport of calcium throughout the body.

The carotenoids lutein, zeaxanthin, lycopene, and beta carotene are oil-soluble and are believed to provide antioxidant properties, possibly in part by activating Nrf2, a cellular regulator of antioxidant production.

Milk thistle is presently believed to function as an anti-oxidant and an anti-inflammatory. Milk thistle is also reported to increase toxin excretion from the liver.

Vitamins are conventionally introduced to the bloodstream in multiple ways. Vitamins taken orally are adsorbed at different rates due to different factors. For example, on average about 10% to 20% of a solid vitamin tablet taken orally is adsorbed. This can be increased to about 30% with an orally taken gel capsule and to about 50% with a conventional intra-oral (sublingual). Injections provide from approximately 90% to 100% adsorption, but are not commonly used for vitamins unless a deficiency has caused acute illness.

While injections provide immediate and nearly total adsorption into the bloodstream, unless the injection is continued for an extended period, thus becoming an infusion, the timeframe in which the vitamins are available to the living cells may be limited. If the living cells can only adsorb a relatively low amount of the vitamin per unit time, the high, but time limited vitamin concentration in the blood may not translate into the desired cellular concentration of the vitamin.

The health benefits of supplying larger doses of vitamins and minerals to the bloodstream than available through conventional oral formulations have been recognized for over 30 years. The most documented history likely surrounds the "Myers cocktail", which has been developed and used since at least the 1960's. The cocktail was successfully used to treat and control chronic problems including fatigue, depression, chest pain, and heart palpitations. More recent formulations of the cocktail have been used to successfully treat asthma, acute migraines, chronic fatigue syndrome, fibromyalgia, acute muscle spasm, upper respiratory tract infections, chronic sinusitis, and seasonal allergies. The Myers cocktail generally includes magnesium chloride, calcium gluconate, calcium pantothenate, Vitamin C, and some B vitamins.

Intravenous (IV) administration of the Myers cocktail achieves blood serum vitamin concentrations not possible with conventional oral administration. For example, with Vitamin C a blood concentration limitation exists irrespective of the oral dose. As the oral dose of Vitamin C is increased, the blood serum concentration of Vitamin C approaches an upper limit due to gastrointestinal saturation and a marked increase in urinary excretion. For example, when daily Vitamin C intake was increased from 200 mg/day to 2,500 mg/day, the plasma concentration only increased by 25%, from 1.2 mg/dL to 1.5 mg/dL. The highest blood serum Vitamin C level observed after oral administration of pharmacological doses was 9.3 mg/dL. In contrast, IV administration of 50 g/day of Vitamin C provided a mean peak plasma level of 80 mg/dL. Similarly, conventional oral administration of magnesium results in little or no change in blood serum magnesium concentration, while IV administration can double or triple the serum levels for short periods of time.

The concentration of nutrients available to the cells, thus blood serum levels, significantly affect the effect of the nutrients on the cells. For example, the antiviral effect of Vitamin C has been demonstrated at a concentration of 10-15 mg/dL in blood serum, a concentration that is not achievable through conventional oral administration. Thus, the IV administration of nutrients, through the production of a marked, though short-lived, increase in blood serum concentration, is believed to provide a window of opportunity for ailing cells to take up needed nutrients. It has been demonstrated that patients who receive a series of IV injections become progressively healthier, and after becoming healthier, the interval between injections can be increased until they are no longer needed.

FIG. 1A and FIG. 1B represent a liposome 100 having a double wall (bilayer) of phospholipids formed from a hydrophilic exterior wall 120 and a hydrophilic interior wall 125. The interior of the double wall 110 is hydrophobic. The hydrophilic interior wall 125 forms a capsule interior 130, to form what may be referred to as a "water-core" liposome. Liposomes may be thought of as small, fluid-filled capsules where the wall of the capsule is formed from two layers of a phospholipid. As phospholipids make up the outer membranes of living cells, the liposome 100 can be thought of as having an outer, permeable membrane wall like a cell, but without a nucleus or the other components of a living cell within the capsule interior 130. The outer and inner walls 120, 125 of the represented liposome 100 are water-soluble, while the interior of the wall 125 is fat-soluble. A common phospholipid used to form liposomes is phosphatidylcholine (PC), a material found in lecithin.

When introduced to the body, liposomes are known to deliver their internal contents to living cells through one of four methods: adsorption, endocytosis, lipid exchange, and fusion. In adsorption, the outer wall of the liposome sticks to the living cell and releases its contents through the outer wall of the living cell into the living cell. In endocytosis, the living cell consumes the liposome, thus bringing the entire liposome into the cell. The cell then dissolves the outer wall of the liposome and releases the liposome contents into the interior of the living cell. In lipid exchange, the liposome opens in close proximity to the living cell and the living cell takes in the localized high concentration of liposome interior. In fusion, the outer wall of the liposome becomes part of the outer wall of the living cell, thus carrying the contents of the liposome into the enlarged living cell. These pathways allow for a potential 100% transfer of the interior contents of the liposome to the interior of the living cell, if the liposome can be brought into close proximity to the cell and is properly constructed to interact with the target cell.

FIG. 2 represents a flattened side view of the double wall (bilayer) of phospholipids that forms the liposome. The phospholipids have polar, hydrophilic "heads" and less polar, relatively hydrophobic "tails". In this representation, the heads form the top and bottom of the bilayer, with the tails forming the interior middle. Oil-soluble compounds can reside between the top and bottom layers within the interior area occupied by the tails.

FIG. 3 represents a micelle 300 having a single wall of phospholipids (monolayer) forming a hydrophilic exterior 320 and a hydrophobic interior 310 lacking the hydrophilic capsule interior of a liposome. Thus, in relation to a liposome, a micelle lacks a bilayer and does not provide the capsule interior that can contain a water-soluble, hydrophilic core composition. The micelle 300 may be thought of as the outer wall of a liposome without the inner wall providing for a capsule interior. Polyethylene glycol modified vitamin E, such as tocopheryl polyethylene glycol succinate 1000 (TPGS), may be used to form micelles in water as the TPGS has a water-soluble head and an oil-soluble tail.

FIG. 4 represents a monolayer surfactant where the oil component is associated with the hydrophobic tails of a surfactant. In this representation, the surfactant has formed a circular shape, thus encircling the oil component and approximating a relatively large, expanded micelle, but that is not required for the oil component to associate with the hydrophobic tails.

The present invention avoids or ameliorates at least some of the disadvantages of conventional oral and intravenous delivery systems for nutrient supplementation of a living organism.

SUMMARY

In one aspect, the invention provides an aqueous, intra-oral, transparent nanoemulsion blend for delivering oil- and water-soluble components of a vitamin supplement to the cells of a mammal when orally administered, where the blend includes a Vitamin C delivery means for delivering the Vitamin C to the bloodstream of the mammal, where the Vitamin C delivery means comprises at least one amphiphilic fat chosen from glycerophospholipids, phosphatidylcholine, phosphatidylethanolamine, phosphatidylinositol, and phosphatidic acid; a Vitamin B complex delivery means for delivering the Vitamin B complex to the bloodstream of the mammal, where the Vitamin B delivery means comprises at least one amphiphilic fat chosen from glycerophospholipids, phosphatidylcholine, phosphatidylethanolamine, phosphatidylinositol, and phosphatidic acid; and an oil-soluble vitamin and oil-soluble carotenoid delivery means for delivering oil-soluble vitamins and oil-soluble carotenoids to the bloodstream of the mammal, where the oil-soluble carotenoid delivery means comprises at least one amphiphilic fat chosen from glycerophospholipids, phosphatidylcholine, phosphatidylethanolamine, phosphatidylinositol, and phosphatidic acid, where the blend has an average particle diameter from 10 to 100 nanometers and is a stable dispersion.

In another aspect of the invention, there is an aqueous, intra-oral, transparent nanoemulsion blend for delivering oil- and water-soluble components of a vitamin supplement to the cells of a mammal when orally administered, where the blend includes at least two different bilayer water-core liposomes, where a first bilayer water-core liposome comprises at least one amphiphilic fat chosen from glycerophospholipids, phosphatidylcholine, phosphatidylethanolamine, phosphatidylinositol, and phosphatidic acid, ethanol, and glycerin, where a capsule interior of the first bilayer water-core liposome comprises Vitamin C dissolved in water, and a second bilayer water-core liposome comprising at least one amphiphilic fat chosen from glycerophospholipids, phosphatidylcholine, phosphatidylethanolamine, phosphatidylinositol, and phosphatidic acid, a first polyethylene glycol surfactant form, ethanol, and glycerin, where a capsule interior of the second bilayer water-core liposome comprises a Vitamin B complex dissolved in water; at least one monolayer surfactant bound particle, where the at least one monolayer surfactant bound particle comprises at least one amphiphilic fat chosen from glycerophospholipids, phosphatidylcholine, phosphatidylethanolamine, phosphatidylinositol, and phosphatidic acid, a second polyethylene glycol surfactant form, an associating oil, oil-soluble vitamins, and oil-soluble carotenoids; and a continuous phase comprising water, glycerin, and ethanol, where the first bilayer water-core liposome, the second bilayer water-core liposome, and the at least one monolayer surfactant bound particle have average particle diameters from 10 to 60 nanometers in the continuous phase, and, where the blend is a stable dispersion.

Other systems, methods, features and advantages of the invention will be, or will become, apparent to one with skill in the art upon examination of the following figures and detailed description. It is intended that all such additional systems, methods, features, and advantages be included within this description, be within the scope of the invention, and be protected by the claims that follow.

The scope of the present invention is defined solely by the appended claims and is not affected by the statements within this summary.

BRIEF DESCRIPTION OF THE FIGURES

The invention can be better understood with reference to the following drawings and description. The components in the figures are not necessarily to scale and are not intended to accurately represent molecules, emphasis instead being placed upon illustrating the principles of the invention.

DETAILED DESCRIPTION

Figure 1A:
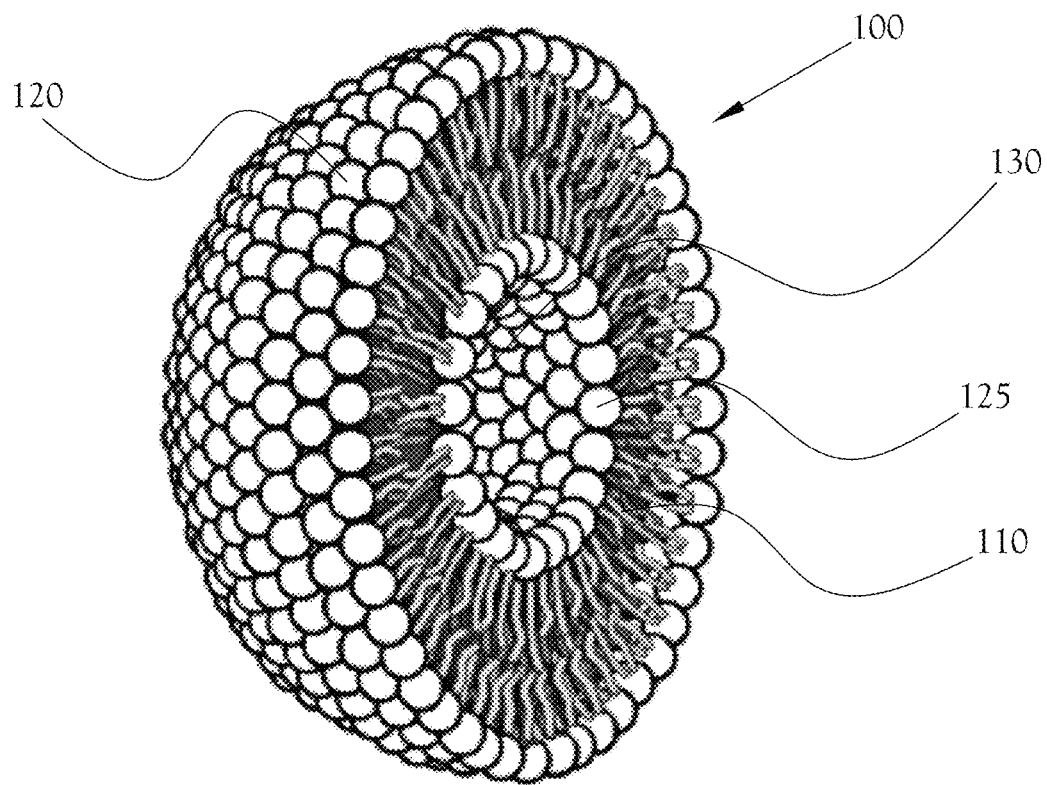
FIG. 1A and FIG. 1B represent a liposome having a double wall of phospholipids forming a hydrophilic exterior and capsule interior with a hydrophobic wall interior.
Figure 1B:
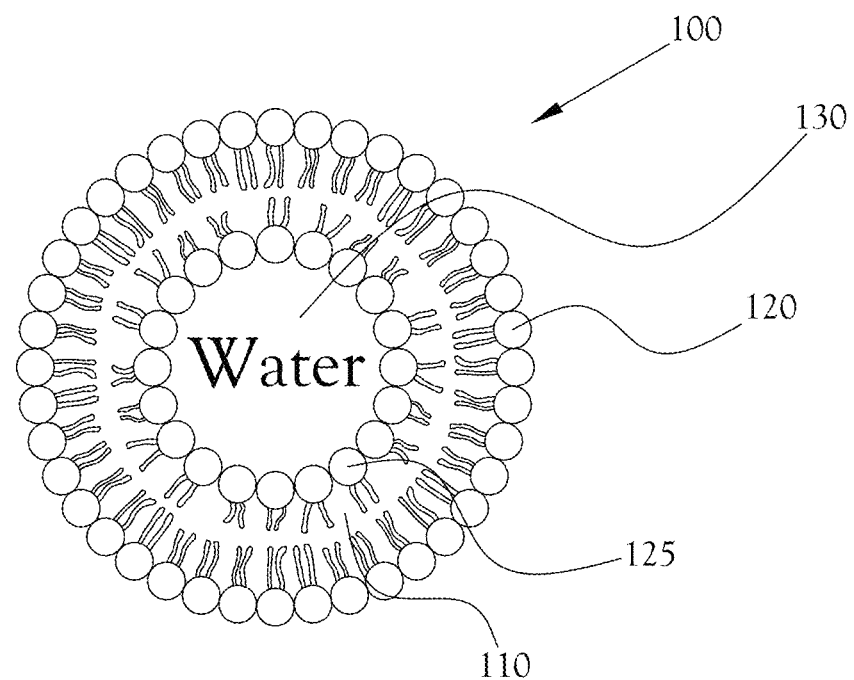
Figure 2:
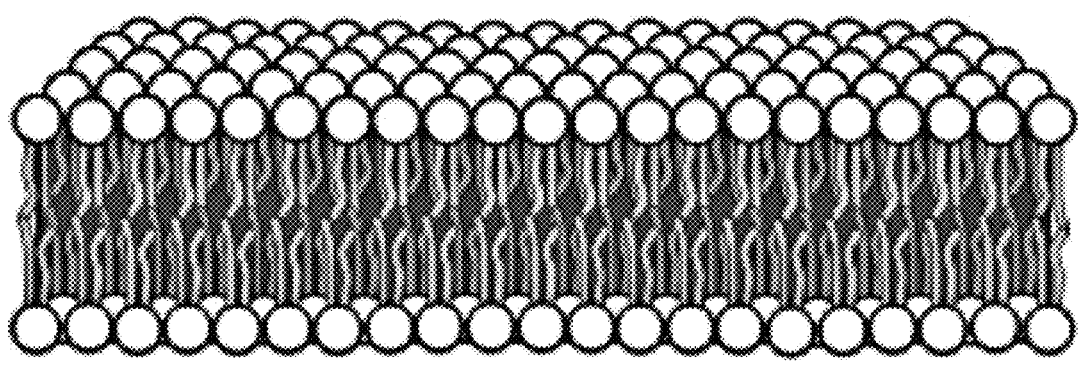
FIG. 2 represents a flattened side view of the double wall (bilayer) of phospholipids that forms the liposome.
Figure 3:
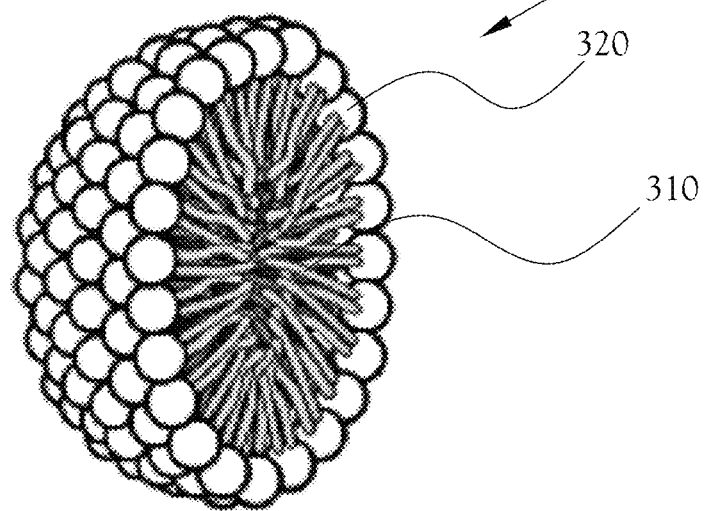
FIG. 3 represents a micelle having a single wall of phospholipids (monolayer) forming a hydrophilic exterior and a hydrophobic interior lacking the capsule interior of a liposome.
Figure 4:
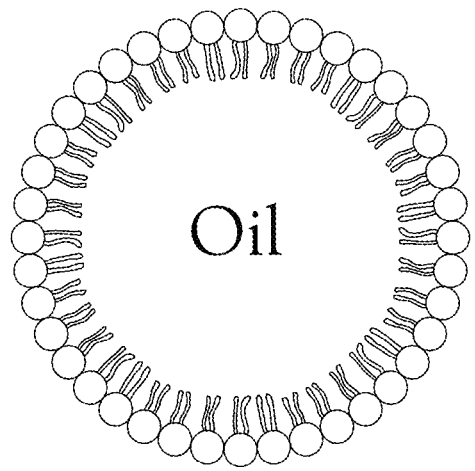
FIG. 4 represents a monolayer surfactant where the oil component is associated with the hydrophobic tails of the surfactant.

An aqueous, intra-oral, transparent nanoemulsion blend in the form of a stable dispersion is provided that delivers both oil- and water-soluble components of a vitamin supplement in the desired concentrations to the cells of a mammal when orally administered. The transparent nanoemulsion blend includes at least two different bilayer water-core liposomes and at least one monolayer surfactant bound particle. The blend optionally may include a micelle formed from phosphatidylcholine (PC).

For the first bilayer water-core liposome, the capsule interior of the liposome includes water and Vitamin C (ascorbic acid), but also may include ethanol and glycerin. The first liposome capsule interior is formed from a bilayer of PC. While a polyethylene glycol surfactant form and/or glycerin may be present in the liposome structure, the PC is the major component of the liposome bilayer.

Being water-soluble, Vitamin C may be carried in the continuous water phase of the transparent nanoemulsion blend or associated with the hydrophilic heads of the PC, but is preferably carried in the capsule interior of the first bilayer water-core liposome.

For the second bilayer water-core liposome, the capsule interior of the liposome includes water, a Vitamin B complex, and betaine (trimethyl glycine), but also may include milk thistle extract, EDTA, ethanol, and glycerin. The second liposome capsule interior is formed from a bilayer of PC and a polyethylene glycol surfactant form. While glycerin also may be present in the liposome structure, the PC is the major component of the liposome bilayer.

Being water-soluble, the Vitamin B complex, betaine, EDTA, ethanol, and glycerin may be carried in the continuous water phase of the transparent nanoemulsion blend or associated with the hydrophilic heads of the PC and/or polyethylene glycol surfactant form, but are preferably carried in the interior capsule of the second bilayer water-core liposome.

The at least one monolayer surfactant bound particle of the transparent nanoemulsion blend is an oil-in-water stable dispersion where the oil component of the particle is associated with the surfactant system. The oil component of the particle includes the oil-soluble vitamin supplement component combined with an associating oil that assists in associating the oil-soluble components of the vitamin supplement with the surfactant system. The associating oil is selected from the group consisting essentially of medium chain triglycerides (MCT), citrus oil, and combinations thereof. The oil component of the at least one monolayer surfactant bound particles is associated with the PC and the polyethylene glycol surfactant form. The surfactant bound particles of the transparent nanoemulsion blend are held in a continuous water phase.

Whether the particles of the transparent nanoemulsion blend are bilayer water-core liposomes or monolayer surfactant bound particles, the particles have an average diameter from 10 to 100 nanometers (nm), preferably from 10 to 60 nm, and more preferably from 10 to 50 nm. The 100-nm average diameter upper limit provides transparency to the nanoemulsion and allows the components of the vitamin supplement to transport through the tissues of the mouth, thus avoiding passage to the stomach and the resulting irreversible chemical alteration and deactivation by acid and bile salts.

Intra-oral delivery of the two different liposomes in the transparent nanoemulsion blend in combination with the monolayer surfactant bound particles enables rapid, and substantially simultaneous intra-oral adsorption of both the water-soluble vitamins and of the oil-soluble vitamins and carotenoids into the bloodstream. Thus, intra-oral delivery of the vitamin supplement provided by the liposome and monolayer surfactant bound particle structures in water prevents the extensive metabolism of the constituents of the vitamin supplement observed for conventional, orally-administered vitamin supplements that pass through the gut.

As the vitamins and carotenoids are transferred intraorally to the bloodstream without passing through the gut, substantially enhanced bioavailability is achieved. In fact, the liposomes and accompanying monolayer surfactant bound particles of the transparent nanoemulsion blend approach IV administration in the rate and concentrations at which the constituents of the vitamin supplement are transferred into the bloodstream. As the transparent nanoemulsion blend substantially avoids digestion by the stomach, liver and intestine, the delivered vitamins and carotenoids rapidly enter the bloodstream substantially unaltered. In addition to the advantages of not requiring venipuncture, the transparent nanoemulsion blend may maintain a longer-duration increased concentration of the delivered vitamins and carotenoids in the bloodstream, and thus available to the living cells, without the need for extended IV infusion times.

The vitamins included in the vitamin supplement include Vitamin C, a methyl B complex, Vitamin A including approximately 14% beta-carotene, Vitamin D3, Vitamin E, and Vitamins K1, and K2. Regarding Vitamin E, both the tocopherol and tocotrienol forms are included.

In addition to vitamins, the vitamin supplement also includes carotenoids. The carotenoids preferably include lutein, zeaxanthin, and lycopene; however, additional carotenoids may be included. Milk thistle also may be included in the colloidal vitamin supplement to enhance bile flow.

The first water-core liposome of the transparent nanoemulsion blend carries water-soluble Vitamin C. From 100 to 140 milligrams (mg), preferably from 110 to 130 mg is included per 5 mL of the blend in the form of sodium ascorbate. Other forms of Vitamin C may be used.

The second water-core liposome of the transparent nanoemulsion blend carries a water-soluble methyl B complex and betain. The methyl B complex includes the activated form of B2 (riboflavin 5'-phosphate) with B6 (pyridoxine hydrochloride), B9 folate (as folinic acid), and methylated B12 to provide the complete factors necessary for healthy methylation processes without creating "methyl traps" or hypermethylation symptoms. Folinic acid, a tetrahydrofolic acid derivative, is used to provide a form of folate believed to circumvent genetic issues that affect folate transport, adsorption and proper utilization. Thus, the methyl B complex preferably includes Vitamin B1-B3, B5-B7, B9, and B12. In total, from 40 to 100 mg, preferably from 50 to 80 mg of the methyl B complex is included per 5 mL of the blend. Other sources and ratios of Vitamin B may be used. Anhydrous betaine also is included from 20 to 30 mg, preferably from 23 to 27 mg, per 5 mL of the blend.

Milk thistle extract and ethylenediaminetetraacetic acid (EDTA) also may be included in the second water-core liposome. Preferably, from 5 to 50 mg of the milk thistle extract is included per 5 mL of the blend. When substantially pure milk thistle extract is used, from 5 to 20 mg may be used per 5 mL of the blend.

The at least one monolayer surfactant bound particles include a mixture of the oil-soluble constituents of the vitamin supplement. Thus, the monolayer surfactant bound particles preferably includes a mixture of the carotenoids, Vitamin E, A, D3, K1, and K2 in the associating oil forming the particles.

The oil-soluble carotenoid lutein is included from 2 to 6 mg, preferably from 4 to 5 mg, per 5 mL of the blend. The oil-soluble carotenoid zeaxanthin is included from 0.5 to 0.9 mg, preferably from 0.6 to 0.7 mg, per 5 mL of the blend. The oil-soluble carotenoid lycopene is included from 0.7 to 1.0 mg, preferably from 0.8 to 0.9 mg, per 5 mL of the blend. Hence, these oil-soluble carotenoids constitute from 3.2 mg to 7.9 mg per 5 mL of the blend, preferably from 5.4 mg to 6.6 mg per 5 mL of the blend. Thus, the ratio of these oil-soluble carotenoids in combination to the amount of ethanol in 5 mL of the blend is from 1:63 to 1:313, preferably from 1:76 to 1:185.

The tocotrienol isomers of Vitamin E are believed to demonstrate superior anticancer, immunomodulatory, and neuroprotective properties in relation to their more common tocopherol counterparts. The tocotrienol forms are also believed to target apoptotic regulators, enzymes, and transcription and growth factors more effectively. However, the tocopherol isomers of Vitamin E are believed to provide enhanced antioxidant performance. Both forms of Vitamin E are included in the monolayer surfactant bound particles of the transparent nanoemulsion blend. Total Vitamin E is included from 20 to 50 mg, preferably from 30 to 40 mg, per 5 mL of the blend. The ratio of tocotrienol isomers to tocopherol isomers is from 1:0.5 to 1:3, preferably from 1:1 to 1:2, and more preferably from 1:1.2 to 1:1.6 per 5 mL of the blend.

Vitamin A is included with from 10% to 20% by weight being beta carotene. The Vitamin A is included from 6000 to 9000 IU, preferably from 7000 to 8000 IU, per 5 mL of the blend. Vitamin D3 is included from 2000 to 3000 IU, preferably from 2300 to 2700 IU, per 5 mL of the blend. Vitamin K1 is included from 35 to 55 micrograms (mcg), preferably from 40 to 50 mcg, per 5 mL of the blend. Vitamin K2 is included from 35 to 55 mcg, preferably from 40 to 50 mcg, per 5 mL of the blend.

Phosphatidylcholine (PC) molecules are a subset of the larger set of phospholipids and are commonly used to form liposomes in water. When placed in water without other constituents, the PC forms liposomes. The application of shear forces to the liposomes can reduce the bilayer liposome structures to monolayer structures with an interior core.

PC has a head that is water-soluble and a tail that is much less water-soluble in relation to the head. PC is a neutral lipid, but carries an electric dipole moment of about 10 D between the head and the tail, making the molecule itself polar. While "PC" is used throughout this document for convenience, PC may be substituted with or combined with other amphiphilic fats. Preferable amphiphilic fats are isolated from lecithin, and include glycerophospholipids, phosphatidylcholine, phosphatidylethanolamine, phosphatidylinositol, and phosphatidic acid.

The polyethylene glycol surfactant form preferably is polysorbate 40, polysorbate 60, polysorbate 80, tocopheryl polyethylene glycol succinate 1000 (TPGS), or combinations thereof, with TPGS being more preferred. TPGS is generally considered a surfactant having a non-polar, oil-soluble "Vitamin E" tail and a polar, water-soluble polyethylene glycol head. Depending on the hydrophilic vs. hydrophobic balance of the water-soluble constituent held in the capsule interior of a liposome, different polyethylene glycol surfactant forms may be preferred. When used in combination with PC to form water-core liposomes, the surfactant form is believed to incorporate into the PC bilayer and after liposome formation reduce "leakage" of the capsule interior contents into the continuous phase through the bilayer.

The other constituents include, but not limited to, sodium hydroxide (NaOH), and a desired flavoring. These other constituents are selected to not interfere with the beneficial operation of the vitamin supplement or the physical structure of the transparent nanoemulsion blend.

The following examples illustrate one or more preferred embodiments of the invention. Numerous variations may be made to the following examples that lie within the scope of the invention.

EXAMPLES

Example 1: Constituents of the Aqueous, Intra-Oral, Transparent Nanoemulsion Blend Vitamin Supplement A transparent nanoemulsion blend was prepared having a 5 mL total volume. The blend included approximately 7890 IU of Vitamin A with 14% by weight as beta-carotene, approximately 12.5 mg of Vitamin B1, approximately 7.5 mg of Vitamin B2, approximately 10 mg of Vitamin B3, approximately 25 mg of Vitamin B5, approximately 7.5 mg of Vitamin B6, approximately 0.5 mg of Vitamin B7, approximately 0.5 mg of Vitamin B9, approximately 0.5 mg of Vitamin B12, approximately 120 mg Vitamin C, approximately 2500 IU of Vitamin D3, approximately 34 mg of tocopherol Vitamin E, approximately 0.045 mg of Vitamin K1, approximately 0.045 mg of Vitamin K2, approximately 25 mg of betaine anhydrous, approximately 24 mg of Tocotrienol Vitamin E, approximately 3.4 mg of lutein, approximately 0.68 mg of zeaxanthin, approximately 0.85 mg of lycopene approximately 500 to 1000 mg ethanol, approximately 500 to 2000 mg glycerin, approximately 5 to 20 mg of milk thistle extract, and minor amounts of EDTA, NaOH, and flavoring. Thus, the continuous phase of the blend includes, water, glycerin, and ethanol with an ethanol to glycerin ratio from 1:1 to 1:4. TPGS and citrus oil were included to provide the desired physical structures in the nanoemulsion. In addition to these ingredients, the blend included enough water to provide a total volume of 5 mL.

Example 2: A Method of Making the Aqueous, Intra-Oral, Transparent Nanoemulsion Blend Vitamin Supplement The first water-core liposome was formed by combining sodium ascorbate (approximately 120 mg), PC, optional TPGS, ethanol, and glycerin (approximately 400 mg) in water to form the Vitamin C containing liposomes.

The second water-core liposome was formed by combining the Vitamin B complex (approximately 64 mg), betaine anhydrous (approximately 25 mg), milk thistle extract (approximately 5 to 20 mg), EDTA, PC, TPGS, ethanol, and glycerin in water to form the B complex containing liposomes.

The oil-soluble vitamins and carotenoids were combined in associating oil, and then combined with TPGS, PC, glycerin, and ethanol in water. The mixture was then homogenized to form an emulsion.

The two liposome mixtures and the oil-soluble emulsion were combined and stirred with additional water to an approximate 5 mL volume.

The mixture was then subjected to high pressure homogenization from approximately 100 to 1000 bar to form the aqueous, intra-oral, transparent nanoemulsion blend vitamin supplement.

Example 3: Bioavailability Uptake and Duration

On an empty stomach, a human subject placed 5 mL of a transparent nanoemulsion blend under the tongue. The blend included bilayer liposomes and monolayer surfactant bound particles as previously discussed. It is believed that the bioavailability of the oil-soluble components delivered to the bloodstream via the monolayer surfactant bound particles would be comparable to the bioavailability provided by the bilayer liposomes to the water-soluble components.

The transparent nanoemulsion blend was held under the tongue for approximately 30 seconds to 2 minutes before swallowing. Blood samples were collected before the blend was administered and at varying time intervals between 5 and 50 minutes after administration of the blend for approximately 4 hours. This procedure was repeated for the water-soluble vitamin in approximately 5 mL of water and for the water-soluble vitamin in a conventional amphiphilic fat-based liposome lacking a polyethylene glycol surfactant form. The collected blood samples were analyzed for the concentration of the B12 component of the Vitamin B complex.

Figure 5:
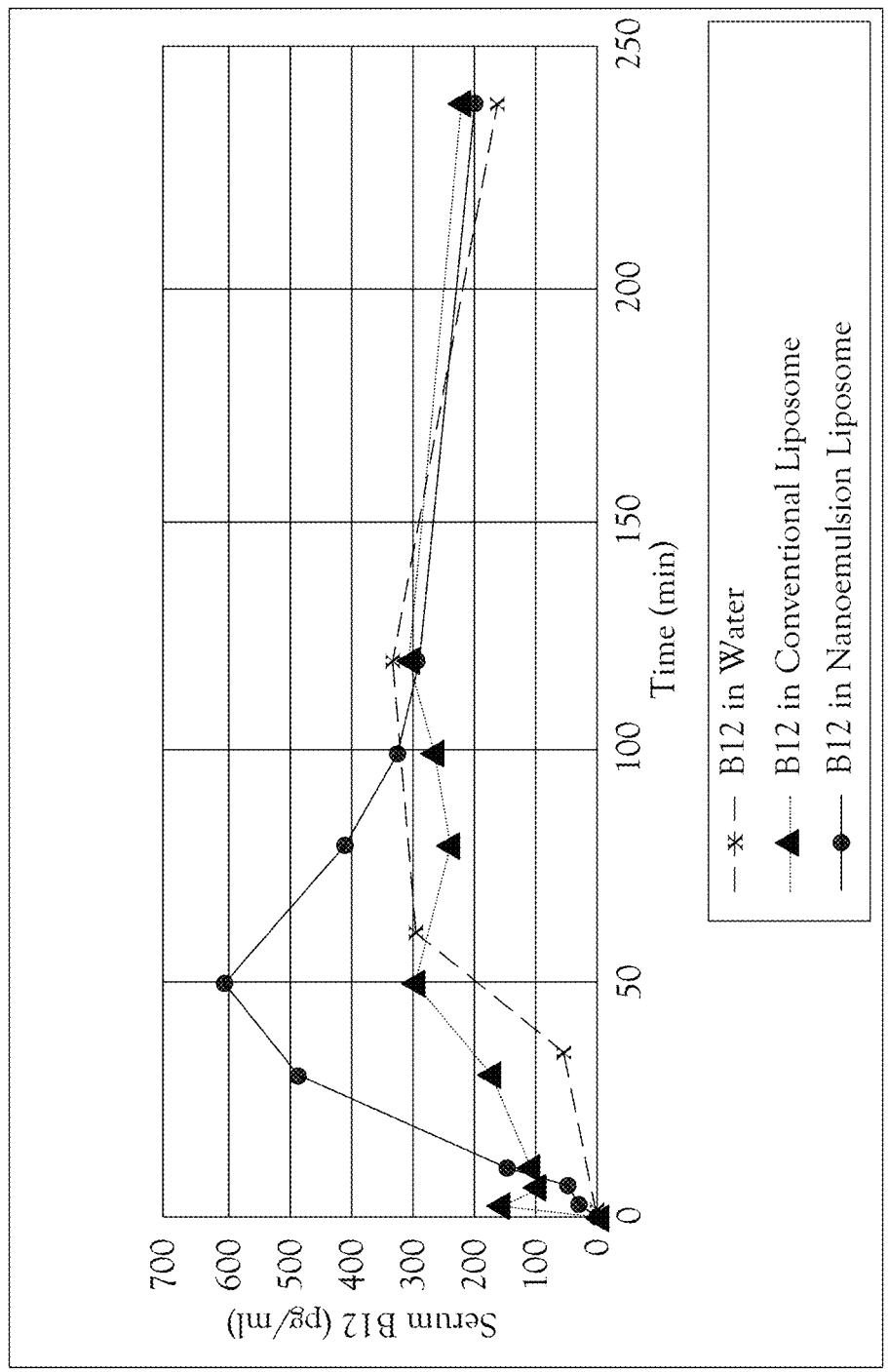
FIG. 5 provides the results of a bioavailability duration analysis in graphical form.

FIG. 5 provides the results of the bioavailability uptake and duration analysis in graphical form. The comparative data establishes that the blend administration provided an approximate doubling of the blood concentration of the water-soluble vitamin 50-minutes post administration in relation to the water and conventional amphiphilic fat-based liposome administered vitamin. The results also establish the enhanced ability of the polyethylene glycol surfactant form in combination with the amphiphilic fat to deliver the Vitamin B complex to the bloodstream. In fact, the bloodstream delivery performance of the conventional amphiphilic fat-based liposome at the 50-minute time interval approximated water for the B12 component of the Vitamin B complex. In addition to the initial and rapid doubling of blood concentration, the blood concentration of the water-soluble vitamin provided by the blend remains substantially above the water and conventional amphiphilic fat-based liposome administered blood concentrations until approximately 100-minutes post administration. The differences in delivery before the 100-minute time are believed attributable to the liposomal particles. Thus, the ability of the transparent nanoemulsion blend to provide vitamin blood concentrations approaching 100% greater than those provided by conventional oral administration methods was established.

To provide a clear and more consistent understanding of the specification and claims of this application, the following definitions are provided.

Intra-oral delivery means that at least 50%, preferably 60%, and more preferably 80% and above of the delivery into the bloodstream that occurs upon oral administration of the liquid including the deliverable occurs by transmucosal absorption through the mouth, throat and esophagus before the liquid reaches the stomach. For particles to be considered suitable for intra-oral delivery, the average particle diameter is at most 125 nm. For example, particles having an average diameter of 100 would have only an approximately 40% delivery to the bloodstream intra-orally, while particles having an average diameter of 75 nm would have and approximate 60% intra-oral delivery to the bloodstream. An 80% or greater intra-oral delivery to the bloodstream may be achieved with an average particle diameter of approximately 50 nm in 0.5 mL liquid after a mouth-residency time of 2 minutes.

Solutions lack an identifiable interface between the solubilized molecules and the solvent. In solutions, the solubilized molecules are in direct contact with the solvent.

Emulsions are mixtures of two or more liquids that do not solubilize. Thus, one of the liquids carries isolated particles in the form of droplets of the other liquid. The particles of one liquid may be said to be dispersed in the continuous phase of the other liquid. An interface, separation, or boundary layer exists between the two liquids, thus between the continuous phase and the particles. Emulsions may be macroemulsions, pseudo-emulsions, microemulsions, or nanoemulsions. The primary difference between the types of emulsions is the size (average diameter) of the particles dispersed in the continuous phase. Macroemulsions and pseudo-emulsions have average particle diameters from 1 to 20 micrometers.

Transparent nanoemulsions have average particle diameters from 10 to 100 nanometers, thus being at least an order of magnitude smaller in average particle diameters than macro- and pseudo-emulsions.

In a continuous water phase, all the water molecules are in direct contact with other water molecules, thus providing a continuously hydrogen bonded system.

A stable dispersion may be determined in one of two ways. One way to establish that a dispersion is stable is when the oil phase particles in a continuous water phase do not change in average diameter by more than +/−20% for a time period of at least 3 months to 3 years, preferably for a time period of at least 6 months to 3 years, and more preferably, for a time period of at least 1 year to 3 years. Another way to establish that a dispersion is stable is when the oil phase particles in the continuous water phase do not separate into a visibly distinct phase with a visible meniscus for a time period of at least 6 months to 3 years, and more preferably, for a time period of at least 1 year to 3 years.

Average particle diameter is determined by dynamic light scattering (DLS), sometimes referred to a photon correlation spectroscopy. The determination is made between 20 and 25 degrees Celsius. One example of an instrument suitable for this determination is a Nicomp 380 ZLS particle sizer as available from Particle Sizing Systems, Port Richey, Fla. DLS can determine the size of particles in a liquid by measuring the intensity of light scattered from the particles to a detector over time. As the particles move due to Brownian motion the light scattered from two or more particles constructively or destructively interferes at the detector. By calculating the autocorrelation function of the light intensity and assuming a particle distribution, it is possible to determine the sizes of particles from 1 nm to 5 um. The instrument is also capable of measuring the Zeta potential of particles.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

While various aspects of the invention are described, it will be apparent to those of ordinary skill in the art that other embodiments and implementations are possible within the scope of the invention.

The invention claimed is:

1. An aqueous, intra-oral, transparent nanoemulsion blend for delivering oil- and water-soluble components of a vitamin supplement to the cells of a mammal when orally administered, the blend comprising:
    Vitamin C and a Vitamin C delivery means for delivering the Vitamin C to the bloodstream of the mammal, where the Vitamin C delivery means comprises at least one amphiphilic fat chosen from glycerophospholipids, phosphatidylcholine, phosphatidylethanolamine, phosphatidylinositol, and phosphatidic acid, where the Vitamin C delivery means further comprises ethanol and glycerin and where a capsule interior of the Vitamin C delivery means comprises the Vitamin C dissolved in water;
    Vitamin B complex and a Vitamin B complex delivery means for delivering the Vitamin B complex to the bloodstream of the mammal, where the Vitamin B complex delivery means comprises at least one amphiphilic fat chosen from glycerophospholipids, phosphatidylcholine, phosphatidylethanolamine, phosphatidylinositol, and phosphatidic acid, where the Vitamin B complex delivery means further comprises ethanol and water and where a capsule interior of the Vitamin B complex delivery means comprises the Vitamin B complex dissolved in water-;
    at least one oil-soluble vitamin;
    at least one oil-soluble carotenoid; and
    an oil-soluble vitamin and oil-soluble carotenoid delivery means for delivering the at least one oil-soluble vitamin and the at least one oil-soluble carotenoid to the bloodstream of the mammal,
        where the oil-soluble vitamin and oil-soluble carotenoid delivery means comprises at least one amphiphilic fat chosen from glycerophospholipids, phosphatidylcholine, phosphatidylethanolamine, phosphatidylinositol, and phosphatidic acid, and
        where the blend has an average particle diameter from 10 to 60 nanometers and is a stable dispersion.

2. The blend of claim 1, where when the blend is administered intra-orally to the mammal, the Vitamin C delivery means, the Vitamin B complex delivery means, and the oil-soluble vitamin and oil-soluble carotenoid delivery means in combination deliver at least 60% of the Vitamin C, the Vitamin B complex, the at least one oil-soluble vitamin, and the at least one oil-soluble carotenoid to the bloodstream of the mammal by transmucosal absorption through the mouth of the mammal.

3. The blend of claim 1, where when the blend is administered intra-orally to the mammal, the Vitamin C delivery means, the Vitamin B complex delivery means, and the oil-soluble vitamin and oil-soluble carotenoid delivery means in combination deliver at least 80% of the Vitamin C, the Vitamin B complex, the at least one oil-soluble vitamin, and the at least one oil-soluble carotenoid to the bloodstream of the mammal by transmucosal absorption through the mouth of the mammal.

4. The blend of claim 1, where the Vitamin C comprises sodium ascorbate and comprises from 100 to 140 mg per 5 mL of the blend.

5. The blend of claim 1, where the Vitamin B complex delivery means further comprises anhydrous betaine.

6. The blend of claim 5, where the anhydrous betaine comprises from 20 to 30 mg per 5 mL of the blend.

7. The blend of claim 1, where the Vitamin B complex is a methyl B complex comprising Vitamins B1-B3, B5-B7, B9, and B12.

8. The blend of claim 1, where the Vitamin B complex comprises from 40 to 100 mg per 5 mL of the blend.

9. The blend of claim 1, where the Vitamin B complex delivery means further comprises milk thistle extract.

10. The blend of claim 1, where the at least one oil-soluble vitamin comprises at least one tocotrienol isomer of Vitamin E and at least one tocopherol isomer of Vitamin E.

11. The blend of claim 10, where the at least one tocotrienol isomer of Vitamin E and the at least one tocopherol isomer of Vitamin E comprise from 20 to 50 mg per 5 mL of the blend.

12. The blend of claim 10, where the at least one tocotrienol isomer of Vitamin E and the at least one tocopherol isomer of Vitamin E are present in a ratio from 1:0.5 to 1:3.

13. The blend of claim 1, where the at least one oil-soluble vitamin comprises Vitamin K1 and Vitamin K2.

14. The blend of claim 13, where the Vitamin K1 comprises from 35 to 55 mcg per 5 mL of the blend and the Vitamin K2 comprises from 35 to 55 mcg per 5 mL of the blend.

15. The blend of claim 1, where the at least one oil-soluble vitamin comprises Vitamin A and Vitamin D3.

16. The blend of claim 15, where the Vitamin A includes from 10% to 20% by weight beta carotene.

17. The blend of claim 1, where the at least one oil-soluble carotenoid is selected from the group consisting of lutein, zeaxanthin, lycopene, and combinations thereof.

18. The blend of claim 1 comprising from 3.2 to 7.9 milligrams of the at least one oil-soluble carotenoid in 5 mL of the blend.

19. The blend of claim 1, where the at least one oil-soluble carotenoid comprises from 2 mg to 6 mg of lutein per 5 mL of the blend.

20. The blend of claim 1, where the at least one oil-soluble carotenoid comprises from 0.7 to 1.0 mg of lycopene per 5 mL of the blend.

21. The blend of claim 1, where the at least one oil-soluble carotenoid comprises from 0.5 mg to 0.9 mg of zeaxanthin per 5 mL of the blend.

22. The blend of claim 1, where the Vitamin C delivery means, the Vitamin B complex delivery means, and the oil-soluble vitamin and oil-soluble carotenoid delivery means are particles having average particle diameters from 10 nm to 50 nm.

23. The blend of claim 1, further comprising a liquid carrier for carrying the Vitamin C delivery means, the Vitamin B complex delivery means, and the oil-soluble vitamin and oil-soluble carotenoid delivery means.

24. The blend of claim 23, where the liquid carrier comprises water, glycerin, and ethanol.

25. The blend of claim 24, where the liquid carrier comprises an ethanol to glycerin ratio from 1:1 to 1:4.

26. The blend of claim 24, where the ratio of the at least one oil-soluble carotenoid to the ethanol is from 1:63 to 1:313 in the blend.

27. An aqueous, intra-oral, transparent nanoemulsion blend for delivering oil- and water-soluble components of a vitamin supplement to the cells of a mammal when orally administered, the blend comprising:
at least two different bilayer water-core liposomes, where
a first bilayer water-core liposome comprises at least one amphiphilic fat chosen from glycerophospholipids, phosphatidylcholine, phosphatidylethanolamine, phosphatidylinositol, and phosphatidic acid, ethanol, and glycerin, where a capsule interior of the first bilayer water-core liposome comprises Vitamin C dissolved in water, and
a second bilayer water-core liposome comprising at least one amphiphilic fat chosen from glycerophospholipids, phosphatidylcholine, phosphatidylethanolamine, phosphatidylinositol, and phosphatidic acid, a first polyethylene glycol surfactant form, ethanol, and glycerin, where a capsule interior of the second bilayer water-core liposome comprises a Vitamin B complex dissolved in water;
at least one monolayer surfactant bound particle, where
the at least one monolayer surfactant bound particle comprises at least one amphiphilic fat chosen from glycerophospholipids, phosphatidylcholine, phosphatidylethanolamine, phosphatidylinositol, and phosphatidic acid, a second polyethylene glycol surfactant form, an associating oil, oil-soluble vitamins, and oil-soluble carotenoids; and
a continuous phase comprising water, glycerin, and ethanol,
where the first bilayer water-core liposome, the second bilayer water-core liposome, and the at least one monolayer surfactant bound particle have average particle diameters from 10 to 60 nanometers in the continuous phase, and,
where the blend is a stable dispersion.

28. The blend of claim 27, where the Vitamin C comprises sodium ascorbate and comprises from 100 to 140 mg per 5 mL of the blend.

29. The blend of claim 27, where the capsule interior of the second bilayer water-core liposome further comprises anhydrous betaine.

30. The blend of claim 29, where the anhydrous betaine comprises from 20 to 30 mg per 5 mL of the blend.

31. The blend of claim 27, where the Vitamin B complex is a methyl B complex comprising Vitamins B1-B3, B5-B7, B9, and B12.

32. The blend of claim 27, where the Vitamin B complex comprises from 40 to 100 mg per 5 mL of the blend.

33. The blend of claim 27, where the capsule interior of the second bilayer water-core liposome further comprises milk thistle extract and EDTA.

34. The blend of claim 27, where the oil-soluble vitamins of the at least one monolayer surfactant bound particle comprise at least one tocotrienol isomer of Vitamin E and at least one tocopherol isomer of Vitamin E.

35. The blend of claim 34, where the at least one tocotrienol isomer of Vitamin E and the at least one tocopherol isomer of Vitamin E comprise from 20 to 50 mg per 5 mL of the blend.

36. The blend of claim 34, where the at least one tocotrienol isomer of Vitamin E and the at least one tocopherol isomer of Vitamin E are present in a ratio from 1:0.5 to 1:3.

37. The blend of claim 27, where the oil-soluble vitamins of the at least one monolayer surfactant bound particle comprise Vitamin K1 and Vitamin K2.

38. The blend of claim 37, where the Vitamin K1 comprises from 35 to 55 mcg per 5 mL of the blend and the Vitamin K2 comprises from 35 to 55 mcg per 5 mL of the blend.

39. The blend of claim 27, where the oil-soluble vitamins of the at least one monolayer surfactant bound particle comprise Vitamin A and Vitamin D3.

40. The blend of claim 39, where the Vitamin A includes from 10% to 20% by weight beta carotene.

41. The blend of claim 27, where the oil-soluble carotenoids are selected from the group consisting of lutein, zeaxanthin, lycopene, and combinations thereof.

42. The blend of claim 27, where the oil-soluble carotenoids comprise from 3.2 to 7.9 mg per 5 mL of the blend.

43. The blend of claim 27, where the oil-soluble carotenoids comprise from 2 to 6 mg of lutein per 5 mL of the blend.

44. The blend of claim 27, where the oil-soluble carotenoids comprise from 0.7 to 1.0 mg of lycopene per 5 mL of the blend.

45. The blend of claim 27, where the oil-soluble carotenoids comprise from 0.5 to 0.9 mg of zeaxanthin per 5 mL of the blend.

46. The blend of claim 27, where the associating oil is selected from the group consisting of medium chain triglycerides, citrus oil, and combinations thereof.

47. The blend of claim 27, where the at least one amphiphilic fat includes at least 30% phosphatidylcholine by weight.

48. The blend of claim 27, where the first polyethylene glycol surfactant form is selected from the group consisting of tocopheryl polyethylene glycol succinate 1000, polysorbate 40, polysorbate 60, polysorbate 80, and combinations thereof.

49. The blend of claim 27, where the first polyethylene glycol surfactant form is tocopheryl polyethylene glycol succinate 1000.

50. The blend of claim 27, where the second polyethylene glycol surfactant form is selected from the group consisting of tocopheryl polyethylene glycol succinate 1000, polysorbate 40, polysorbate 60, polysorbate 80, and combinations thereof.

51. The blend of claim 27, where the second polyethylene glycol surfactant form is tocopheryl polyethylene glycol succinate 1000.

52. The blend of claim 27, where the first and the second polyethylene glycol surfactant forms are the same.

53. The blend of claim 27, where the first and second bilayer water-core liposomes and the at least one monolayer surfactant bound particle have average particle diameters from 10 to 50 nm.

54. The blend of claim 27, where the continuous phase comprises an ethanol to glycerin ratio from 1:1 to 1:4.

55. The blend of claim 27, where the ratio of the oil-soluble carotenoids to the ethanol is from 1:63 to 1:313 in the blend.

56. The blend of claim 27 where at least 60% of the Vitamin C, the Vitamin B complex, the oil-soluble vitamins, and the oil-soluble carotenoids are delivered to a bloodstream by transmucosal absorption through the mouth, when 0.5 mL of the blend is intra-orally administered to a human for a mouth-residency time of 2 minutes.

57. The blend of claim 27 where at least 80% of the Vitamin C, the Vitamin B complex, the oil-soluble vitamins, and the oil-soluble carotenoids are delivered to a bloodstream by transmucosal absorption through the mouth, when 0.5 mL of the blend is intra-orally administered to a human for a mouth-residency time of 2 minutes.

* * * * *